United States Patent [19]

Förster et al.

[11] E Re. 31,109

[45] Reissued Dec. 21, 1982

[54] SINGLE MAGNETIC STRAY FIELD SENSOR WHOSE SIGNALS ARE DIFFERENTLY ATTENUATED IN TWO CHANNELS AND THEN COMPARED

[76] Inventors: Friedrich M. O. Förster, In Laisen 70; Alfons Kalisch, Fliederweg 3, both of D-7410 Reutlingen 1, Fed. Rep. of Germany

[21] Appl. No.: 162,051

[22] Filed: Jun. 23, 1980

Related U.S. Patent Documents

Reissue of:

[64] Patent No.: 4,117,403
Issued: Sep. 26, 1978
Appl. No.: 780,401
Filed: Mar. 23, 1977

[30] Foreign Application Priority Data

Mar. 25, 1976 [DE] Fed. Rep. of Germany ..... 2612697

[51] Int. Cl.[3] ..... G01N 27/82
[52] U.S. Cl. ..... 324/240
[58] Field of Search ..... 324/228, 239, 240, 227, 324/226, 225, 219-221

[56] References Cited

U.S. PATENT DOCUMENTS

| | | | |
|---|---|---|---|
| 2,925,552 | 2/1960 | Cowen et al. | 324/217 |
| 3,271,664 | 9/1966 | Mountz et al. | 324/227 |
| 3,343,079 | 9/1967 | Crouch | 324/227 |
| 3,538,433 | 11/1970 | Wood et al. | 324/227 |

*Primary Examiner*—Gerard R. Strecker
*Assistant Examiner*—Walter E. Snow
*Attorney, Agent, or Firm*—George J. Netter

[57] ABSTRACT

The described tube testing apparatus indicates whether a defect is either external or internal, enabling a quantitative classification of defects and an analog representation on location of the defect in the tube wall. The ratio of the signal levels of a defect is taken as a threshold in two different circuit channels. For tubes of a given wall thickness, the ratio of the defect signal levels resulting in the two channels is a fixed number which is a function of the location of a defect in the tube wall causing a defect signal. Uninfluenced test signal voltages from the first channel are available for further evaluation and are applied to voltage discriminators having various threshold voltages. Since the signal levels for external and internal defects are different, this may be effected separately for external and internal defects, offering the possibility for defect classification adapted to the respective requirements, for example, into large, medium or small external defects, or large, medium or small internal defects.

12 Claims, 4 Drawing Figures

SINGLE MAGNETIC STRAY FIELD SENSOR WHOSE SIGNALS ARE DIFFERENTLY ATTENUATED IN TWO CHANNELS AND THEN COMPARED

Matter enclosed in heavy brackets [ ] appears in the original patent but forms no part of this reissue specification; matter printed in italics indicates the additions made by reissue.

FIELD OF THE INVENTION

The invention relates to method and apparatus for the magnetic defects inspection of tubes according to which the tubes are magnetized and their surfaces are scanned by a probe arrangement for magnetic stray fluxes resulting from defects in the tube wall. The stray flux signals generated in the probe arrangement are fed to first and second channels, the first channel reproducing the stray flux signals of internal defects and external defects approximately at the same level, whereas the second channel reproduces the stray flux signals of internal and external defects at a modified level, and the signals of the two channels are temporarily stored.

PRIOR ART

A method of the aforementioned type is described in U.S. Pat. No. 3,343,079 which deals with the discrimination of internal and external defects, i.e., defects located on the inner and outer surface of a tube, respectively, in the inspection of tubes by magnetic stray flux inspection techniques. According to this patent, a stray flux probe scanning the surface of a pipe is interconnected with two test channels of which the first channel passes signals of internal and external defects without attenuation, whereas the second channel has a high-pass filter to suppress for the most part the signals of internal defects lying in the low-frequency spectrum. The object of this measure is to obtain the signals of the internal and external defects from the first of the two channels and from the second channel only signals from the external defects.

In both channels the signals are fed to one comparator each, which compares them with an adjustable reference voltage. In the first channel the level of the reference voltage corresponds to the level of the defect signal of maximum permissible internal defect, while in the second channel, it corresponds to the level of the maximum permissible external defect. In case a defect signal exceeds the pre-selected level of the reference voltage at the input of the comparator, there will be a binary signal at the output of this comparator which indicates the presence of a non-permissible defect. To each of the two comparators a binary storage element is connected which is capable of temporarily storing defect signals. The latter is necessary because the stray flux signals at the outputs of the two channels do not occur simultaneously, but at different times due to the filtering. The outputs of the storage elements are fed into two AND gates such that a binary signal occurs at the output of the first AND gate only if the storage elements of both channels are set (i.e., if they supply a binary defect signal), and that a binary signal occurs at the output of the second AND gate only if the storage element of the first channel is set and the storage element of the second channel is not set. This insures that at the output of the first AND gate only the defect signal resulting from external defects exists, and at the output of the second AND gate only the signals resulting from internal defects are transmitted.

Admittedly, the patented arrangement can be advantageously operated in the manner described; however, it has a number of serious disadvantages which hitherto prevented a practical application and which will be explained in the following. In generally used stray flux probes of a simple construction, internal defects frequently generate considerably lower signals than external defects when the probes scan the outer surface of a tube. This is simply due to the lower density of the stray flux of an internal defect on the outer tube surface as compared to that of an external defect. For the patented method, this phenomenon which is one of the causes for the interest in the discrimination of signals of internal and external defects, results in a small external defect which does not yet exceed the threshold of the second channel set for the external defect, may exceed the threshold of the first channel set for internal defects. This results in an "internal defect" signal being erroneously transmitted, although there is no internal defect.

An ideal separation of the signals of internal and external defects by the described means, i.e., a high-pass filter, is unfortunately not possible, since the differences of the frequency spectra of the respective signals are not as large as would be desirable in this case. The application of filters having very steep wave edge characteristics for the suppression of signals of internal defects cannot be justified either, since in this case signals of external defects would also inadmissably be clipped in their frequency characteristic. Hence, it follows that, in practice, the signals of very large internal defects can also penetrate in the first channel and exceed the threshold for external defects and in that way simulate the presence of an external defect.

Another great disadvantage of the described method consists in that minor and major internal or external defects cannot be discriminated and that the setting of additional thresholds is not easily accomplished. On the other hand, however, it is the discrimination of major and minor defects that is an important object of considerable economical significance, for it is a precondition for the decision whether a test specimen can be reworked or must be scrapped.

Finally, it should also be mentioned that a precondition for the described method is that only internal or external defects occur. In case a defect is located within the tube wall without breaking through the outside or inside surface, or in case internal and external defects occur at the same time, an unequivocal indication is by no means possible.

SUMMARY OF THE INVENTION

In view of the mentioned disadvantages of the above described method, an object of the invention is the provision of method and apparatus for insuring a correct determination of whether an "internal defect" or "external defect" exists, which makes a quantitative classification of defects possible and which also enables an analog statement on the location of the defect in the tube wall to be made.

Instead of starting from internal and external defects of a given signal level in the assessment of a location of a defect, as has hitherto been the practice, in the practice of this invention the ratio of the signal levels of a defect is taken as a basis or threshold in two different channels. In this way, the method is applicable to a further range of defects, independent of their size. For tubes of a given wall thickness, the ratio of the defect signal levels resulting in the two channels is a fixed number which is a function of the location of a defect in the tube wall causing a defect signal. If this ratio is, for example, 1 for an external defect and 2 for an internal defect, the decision whether a defect is to be valued as an external defect or an internal defect can be made at any point between the two numbers 1 and 2. Therefore, the limit in the tube wall which is relevant for this decision is determined.

Uninfluenced test signal voltages from the first channel are available for further evaluation and are applied to voltage discriminators having various threshold voltages. Since the signal levels for external and internal defects are different, this may be effected separately for external and internal defects. This offers the possibility for a defect classification adapted to the respective requirements, for example, into large, medium or small external defects, or large, medium or small internal defects.

DESCRIPTION OF A PREFERRED EMBODIMENT

Figure 1:
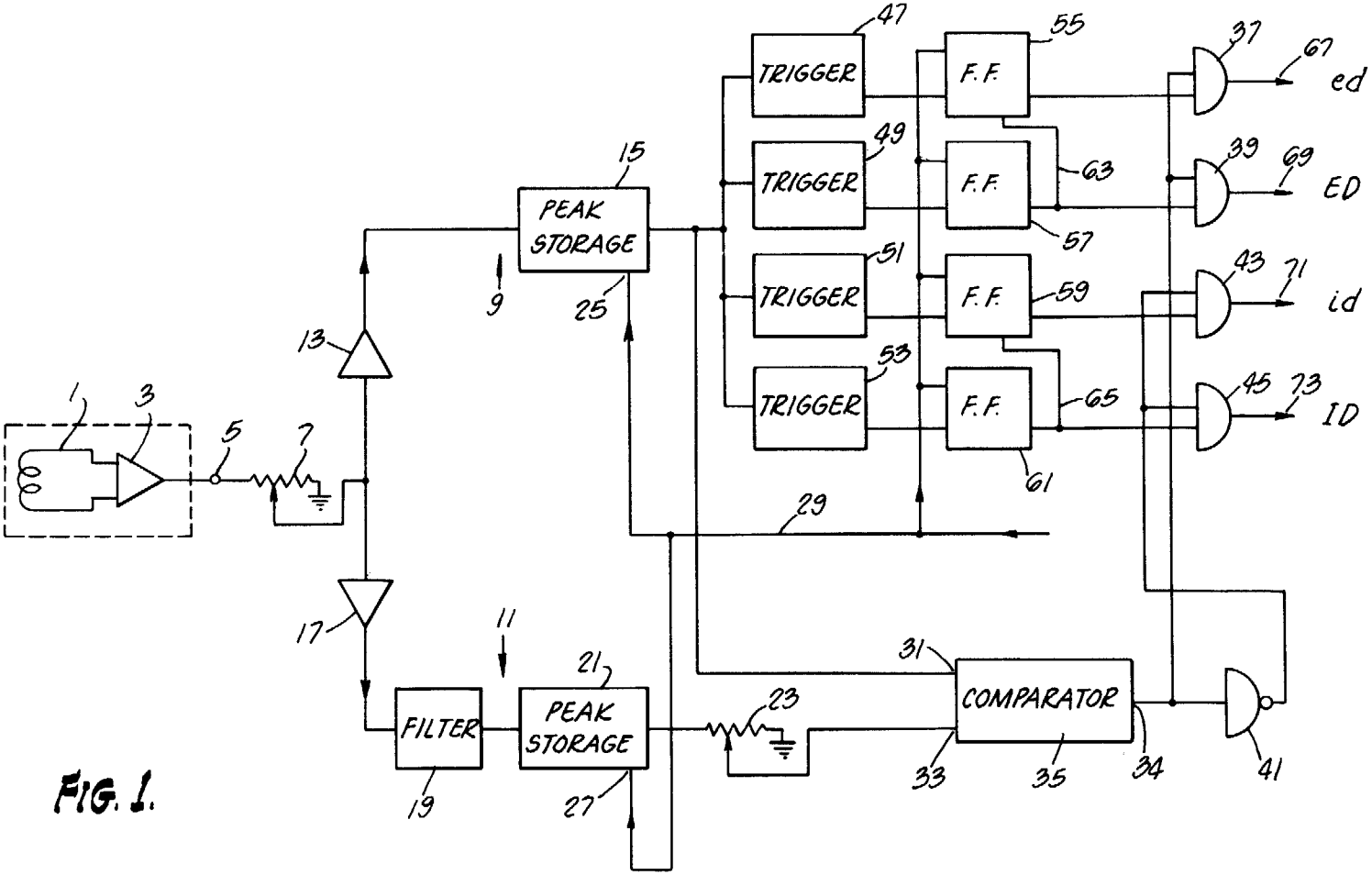
FIG. 1 is a function block circuit diagram of a testing device.

FIG. 1 shows a circuit diagram of a testing device to be described herein, which can be used for the determination of internal and external defects in tubes. For this purpose, the tube to be inspected is magnetized in a known manner, for example by a magnet yoke installed in a rotating test head between the pole shoes of which a probe 1 is additionally arranged to scan the outer surface of the tube for stray flux. A preamplifier 3 rotating together with probe 1 amplifies the stray flux signals induced in the probe 1 in case tube wall when defects are present.

The amplification produced by preamplifier 3 raises the signal to a level sufficiently above the interference level to be expected in case of signal retransmission. Signals are supplied from the rotating test head to the outside via sliding contacts 5. The sensitivity required for a testing situation is set by means of an input voltage divider 7, the output of which leads to two test channels 9 and 11, the first one consisting of an amplifier 13 and a peak value storage element 15, and the second one including an amplifier 17, a high-pass filter 19, a peak value storage element 21, and a voltage divider 23. The high-pass filter has the characteristic that the frequency spectrum of the stray flux signal of an external defect is essentially allowed to pass, whereas the stray flux signal of an internal defect is largely suppressed. Instead of the high-pass filter in channel 11, a low-pass filter can also be used, which was not possible according to the known method described earlier herein. In any case, it is important that the attenuation of the signals of internal defects in channel 11 is, as far as possible, different from the attenuation of the signals of external defects.

It is the purpose of the two peak value storage elements 15 and 21 to retain the maximum values of the stray flux signal which, due to the filter 19, are not simultaneously available in the two channels 9 and 11 over a given period so that they can be compared with one another. For resetting, the two peak value storage elements 15 and 21 are provided with resetting inputs 25 and 27 to which a reset signal is supplied via line 29 when the storage time is to be terminated.

The signal levels in the two channels 9 and 11 are balanced relative to one another by means of voltage divider 23. The outputs of the two channels 9 and 11 are connected with the inputs 31 and 33 of a comparator circuit 35, the operation of which will be explained in more detail later.

Only a brief description of the operation of the comparator circuit 35 will be given, since it is a well-known apparatus. If the inputs 31 and 33 supply signals of an internal defect (ID) taken from the channels 9 or 11, a binary signal "0" is obtained at the output 34 of the comparator circuit 35. However, if the two inputs 31 and 33 supply the signals of an external defect (ED), a binary signal "1" is obtained at output 34. The output 34 of the comparator circuit 35 is directly connected to, respectively, one input of each of two AND gates 37 and 39, and via an inverter 41 to, respectively, one input each of two AND gates 43 and 45.

A chain of triggers 47, 49, 51 and 53 is connected to the output of the peak value storage element 15. Basically, the chain may also be either connected to the output of the storage element 15 or to any point leading the signal voltage out of the probe 1, provided that the level of the signal voltage of filter 19 has not been modified. The level of the response thresholds of triggers 47 through 53 can be individually set for each trigger. In the present embodiment, the setting has been selected so that trigger 47 responds to small external defects, trigger 49 to large external defects, trigger 51 to small internal defects, and trigger 53 to large internal defects. The outputs of triggers 47–53 are individually connected to the set inputs of bistable storage elements 55, 57, 59 and 61, whereas the reset inputs of the triggers are connected in common to line 29. The outputs of the storage elements 55, 57, 59 and 61 are, respectively, connected to one of the two inputs of the AND gates 37–45. From the outputs of the storage elements 57 or 61, blocking lines 63 and 65 lead back, respectively, to the blocking inputs of the storage elements 55 and 59, and prevent the storage elements 55 and 59 remaining set when the storage elements 57 or 61 have been set.

Due to the linkage of the output signals of triggers 55–61 to the output signals of the comparator circuit 35 via the AND gates 37–45, a binary defect signal is either generated at one of the outputs 67, 69 or the AND gates 37, 39 or at one of the outputs 71, 73 and the AND gates 43, 45, namely at one of the outputs 67, 69, if the comparator circuit has signaled an external defect and at one of the outputs 71, 73 if the comparator circuit has signaled an internal defect. Consequently, the following information classifying the defect sizes can be obtained from the outputs 67–73: small external defect (ed), large external defect (ED), small internal defect (id), or large internal defect (ID). In contrast to the known method of the patent described earlier herein, this present method permits optional setting of the defect thresholds both for internal defects and for external defects.

Figure 2:
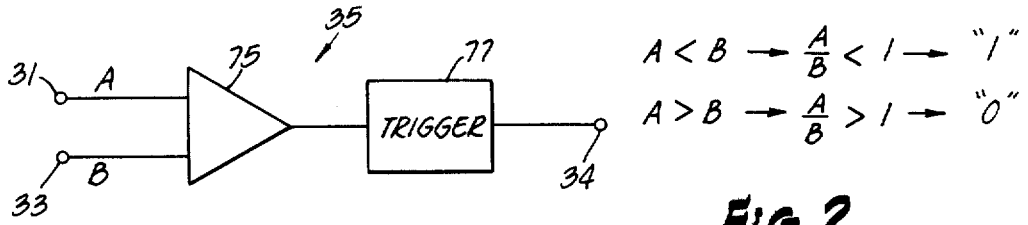
FIGS. 2, 3 and 4 show alternatives for a part of the circuit diagram.

In the following, some alternative embodiments of circuits 35 by means of which the signal voltages of the two channels 9 and 11 can be compared are described. FIG. 2 shows one such possibility in which the comparator circuit 35 consists of a high-gain differential amplifier 75, the inputs 31 and 33 of which are connected to the outputs of channels 9 or 11, and the output of which is fed into a trigger 77. The amplifier 75 is designed so that only two stable states of its outputs are possible, namely, full negative modulation if the signal A at the input 31 is smaller than the signal B at the input 33, and full positive modulation if the signal A at the input 31 is larger than the signal B at the input 33. The function of the trigger 77 is merely to convert the connection states of the amplifier 75 into system-conforming signals "1" and "0" for the AND gates. Consequently, the decision "external defect—internal defect" is made if the ratio of the signal amplitudes at the inputs 31, 33 is not unity, i.e., A/B 1.

As has already been mentioned for a given tube wall thickness, the ratio of the output signals of channel 9 to the output signals of channel 11 depends on the location of a defect in the tube wall due to the modification of the signal by the high-pass filter 19. For example, in a typical case, the ratio of the signals for an internal defect is double the ratio of signals for an external defect. Accordingly, the voltage divider 23 is set so that a ratio of the signal amplitudes of $A/B > 1$ is obtained for internal defects and of $A/B < 1$ for external defects. In this way, the point of the tube wall at which the decision "external defect—internal defect" is made can be determined.

Figure 3:
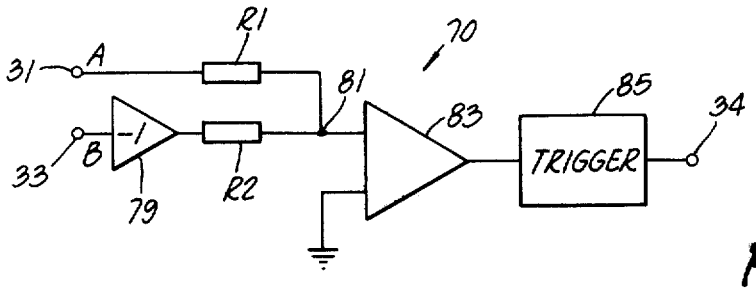

In the comparator circuit 70 according to FIG. 3, signal A is fed via a resistor R1 and signal B, after inversion by an amplifier 79 with a gain $V = -1$, is fed via a resistor R2 to the summing junction 81 of an operational amplifier 83. A trigger 85 is connected to the output of the operational amplifier which generates system-conforming signals "0" and "1." The operational amplifier 83 which is operated without negative feedback is fully modulated as soon as a small voltage in one direction is obtained at the summing junction, whereas any voltage at the summing junction in the opposite direction immediately causes reversed full modulation. If the two resistors R1 and R2 are equal, the comparator 70 operates in the same manner as the previously described comparator circuit 35 according to FIG. 2. If the resistors R1 and R2 are variable, the voltage divider 23 is not required.

Figure 4:
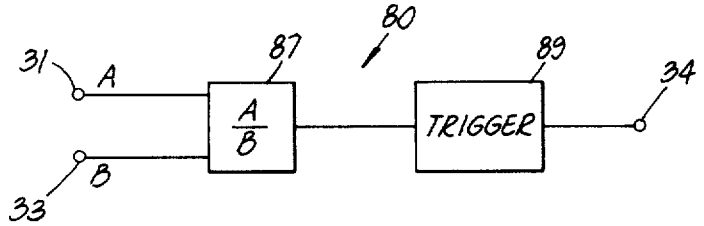

The comparator circuit 80 of FIG. 4 is provided with a quotient generator 87 and a trigger 89 connected thereto. The quotient generator 87 is a known circuit able to generate the quotient A/B of two input signals A and B. The threshold voltage of trigger 89 can be set to any desired value. For example, during operation of this circuit, the voltage divider 23 may be set so that the input signals A and B are equal for an external defect. The quotient A/B at the output of the quotient generator 87 will then assume a value of random defects which corresponds to the location of these defects in the tube wall. Subsequently, the threshold voltage of trigger 89 can be set to a level which is optimal for the decision "external defect—internal defect."

We claim:

1. A method of magnetic defects inspection of tubes in which the tubes are magnetized and the tube surfaces are scanned by a single magnetic sensing element for magnetic stray fluxes resulting from defects in the tube wall, the stray flux signals generated in the single sensing element being fed to first and second channels, of which the first channel passes analog stray flux signals produced by internal defects and external defects, whereas the second channel passes said stray flux signals of internal and external defects attenuated as compared with those occurring in the first channel, and the signals of the two channels are temporarily stored, which comprises:

storing the analog signals of the first and second channels; and comparing the stored signals with one another, the location of the defect in the tube wall generating the defect stray flux being determined by the relative magnitude of said signals.

2. A method as in claim 1, in which comparing is accomplished by forming a ratio of the magnitudes of the signals in the two channels for a given defect in a defined position and determining the value of the ratio.

3. A method as in claim 1, in which, on the basis of the comparison of the stored signals of the two channels, inverse binary signals are generated for "external defect" and "internal defect," respectively.

4. Apparatus for defects testing of metal tube, comprising:

means for magnetizing the tubes;

a single magnetic sensing element scanning the tube surface and producing signals responsive to defects in the tubes;

a first channel connected to the single sensing element, said channel including first signal storage means;

a second channel connected to the single sensing element, said second channel including filter means and a second signal storage means connected with the filter means, said filter attenuating the signals of external defects and internal defects to a different degree; and said signal storage means consisting of analog storage elements and the outputs of the first and second channels being connected to a comparator.

5. Apparatus as in claim 4, in which signal amplitude controlling means are connected into at least one of the channels.

6. Apparatus as in claim 4, in which the comparator includes a high-gain differential amplifier.

7. Apparatus as in claim 4, in which the comparator includes a computing amplifier having a summing junction connected to the output of the first channel via a resistor, and the output of the second channel being connected via an inverting amplifier and a resistor to said summing junction.

8. Apparatus as in claim 4, in which the comparator includes a quotient generator.

9. Apparatus as in claim 8, in which a trigger is connected to the output of the quotient generator.

10. Apparatus as in claim 4, in which the comparator provides a binary output.

11. Apparatus for receiving electric signals from a single magnetic sensing element responsive to changes in flux in a magnetized hollow metal tube produced by defects in said tube and providing signals identifying the location of the defects, comprising:

a first channel interconnected with the single sensing element having, in the order stated, an amplifier and peak signal storage means serially connected;

a second channel interconnected with the single sensing element having, in the order stated, an amplifier, a filter for passing signal frequencies characteristic of tube defects existing adjacent the tube exterior, and a peak signal storage means;

a comparator connected to the first and second channels, said comparator providing a first output when the first channel output exceeds the second channel output, and a second output when the second channel output exceeds the first channel output;

a first AND gate connected to provide an output on coincidence of a first channel output and one of the comparator outputs; and a second AND gate connected to provide an output on coincidence of a first channel output and the other of the comparator outputs.

12. A method of inspecting metal tubes for defects in which the tubes are magnetized and the tube surfaces are scanned by a single magnetic sensing element which produces electric signals responsive to the presence of magnetic stray fluxes at said tube surfaces, said electric signals having first and second frequency ranges characteristic of defects located adjacent the tube exterior and interior, respectively, which comprises the steps of:

passing the stray flux signals along first and second channels to respective outputs;

filtering out one of said first and second frequency ranges in the second channel;

attenuating the transmission of signals differently in the first and second channels;

forming a third signal corresponding to a ratio of the signals at the outputs of the first and second channels;

comparing the third signal with a predetermined standard of magnitude corresponding to unity for the third signal such that identification of the location of the defect producing the stray flux signals as internal or external corresponding to whether the third signal is greater than or less than unity.

* * * * *